(12) United States Patent
Bianchi et al.

(10) Patent No.: US 9,920,067 B2
(45) Date of Patent: Mar. 20, 2018

(54) BIS-THIENOBENZOTHIENOTHIOPHENE COMPOUNDS AND PROCESS FOR THEIR PREPARATION

(71) Applicant: Eni S.p.A., Rome (IT)

(72) Inventors: Gabriele Bianchi, Novara (IT); Giuliana Schimperna, Novara (IT)

(73) Assignee: Eni S.p.A., Rome (IT)

( * ) Notice: Subject to any disclaimer, the term of this patent is extended or adjusted under 35 U.S.C. 154(b) by 0 days.

(21) Appl. No.: 15/535,079

(22) PCT Filed: Dec. 11, 2015

(86) PCT No.: PCT/EP2015/079390
§ 371 (c)(1),
(2) Date: Jun. 12, 2017

(87) PCT Pub. No.: WO2016/092065
PCT Pub. Date: Jun. 16, 2016

(65) Prior Publication Data
US 2017/0342087 A1  Nov. 30, 2017

(30) Foreign Application Priority Data
Dec. 12, 2014 (IT) .............................. MI2014A2128

(51) Int. Cl.
| C07D 495/22 | (2006.01) |
| C07F 7/22 | (2006.01) |
| C07F 5/02 | (2006.01) |
| C07D 271/12 | (2006.01) |
| H01L 51/00 | (2006.01) |
| C09K 11/06 | (2006.01) |

(52) U.S. Cl.
CPC .......... *C07D 495/22* (2013.01); *C09K 11/06* (2013.01); *C09K 2211/1092* (2013.01)

(58) Field of Classification Search
CPC . C07D 495/22; C07F 7/22; C07F 5/02; H01L 51/00
USPC .............. 549/41, 3, 4, 50; 548/126; 313/504
See application file for complete search history.

(56) References Cited

U.S. PATENT DOCUMENTS

2013/0277657 A1  10/2013  Park et al.

FOREIGN PATENT DOCUMENTS

| EP | 1932847 A1 | 6/2008 |
| WO | WO2013098726 A1 | 7/2013 |

OTHER PUBLICATIONS

International Search Report for PCT/EP2015/079390 dated Feb. 8, 2016, 12 pages.

Laure Biniek et al: "New Fused 1-20 Bis-Thienobenzothienothiophene Copolymers and Their Use in Organic Solar Cells and Transistors", Macromolecules, vol. 46, No. 3, Feb. 12, 2013 (Feb. 12, 2013), pp. 727-735.
Takamichi Mori et al: "Consecutive Thiophene-Annulation Approach to [pi]-Extended Thienoacene-Based Organic Semiconductors with [1]Benzothieno[3.2-b ] [1]benzothiophene (BTBT) Substructure", Journal of the American Chemical Society. vol. 135. No. 37. Sep. 18, 2013 (Sep. 18, 2013). pp. 13900-13913.
Toyota Kozo et al: "Preparation of 1.4-bis(3-ethynylthieno[3.2-b]thiophen-2-y l)benzene derivatives as peptide-inspired molecules". Heterocycles : An International Journal for Reviews and Communications in Heterocyclic Chemistry. Japan Institute of Heterocyclic Chemistry.JP. vol. 78. No. 12. Jan. 1, 2009 (Jan. 1, 2009). pp. 3037-3051.
Mullen K. et al : "Tetrathiahexacene as Building Block for Solution-Processable Semiconducting Polymers: Exploring the Monomer Size Limit", "Macromolecules" 2010, vol. p. 6264-6267.
Burton D. J. et al: "Site-Specific Preparation of 2-Carboalkoxy-4-substituted Naphthalenes and 9-Alkylphenanthrenes and Evidence for an Allene Intermediate in the Novel Base-Catalyzed Cyclization of 2-Alkynylbiphenyls", "Organic letters" (2006), vol. 8, No. 23, p. 5295-5298.
Swager T. M. et al: "Direct Electrophilic Cyclizations: Efficient Methodology for the Synthesis of Fused Polycyclic Aromatics", "Journal of the American Chemical Society" (1997), vol. 119, p. 4578-4593.
Rafael Chinchilla and Carmen Nájera (2007) "The Sonogashira Reaction: A Booming Methodology in Synthetic Organic Chemistry" Chem. Rev. American Chemical Society 103 (3): p. 874-922.
Li Y. et al: "Synthesis of a polythieno[3,4-b]thiophene derivative with a low-lying HOMO level and its application in polymer solar cells", "Chemical Communications" (2011), vol. 47, p. 8850-8852.
C. Ko, W.H. Lam, V.W.Yam -Chem. Com. 2008, p. 5203.
Fuller et al. J. Chem. Soc. Perkin Trans. 1, 1997, p. 3465.
M. Turbiez et al. Chem. Comm. 2005, p. 1161.
"β-Alkyl substituted Dithieno[2,3-d;2',3'-d']benzo[1,2-b;4,5-b']dithiophene Semiconducting Materials and Their Application to Solution-Processed Organic Transistors", "Chemistry of Materials" (2010), vol. 24, No. 17, p. 3464-3472.
"Synthesis and Properties of a Series of Well-Defined and Polydisperse Benzo[1,2-b:4,3-bldithiophene Oligomers", "The Journal of Organic Chemistry" (2007), vol. 72, No. 24, p. 9141-9151.
"Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility", "Chemistry of Materia/s" (2012), vol. 24, No. 10, p. 1699-1709.

(Continued)

*Primary Examiner* — Charanjit Aulakh
(74) *Attorney, Agent, or Firm* — Abel Law Group, LLP

(57) ABSTRACT

The present invention relates to bis-thienobenzothienothiophene compounds and a process for their preparation. More in particular, the present invention relates to a new angular bis-thienobenzothienothiophene compound and the process for its preparation wherein said process comprises reacting at least one dihalogenated dithiophene compound with at least one terminal alkyne and the subsequent double annulation reaction. Said bis-thienobenzothienothiophene compounds can be appropriately functionalized and polymerized to produce electron donor compounds that can be advantageously used in the construction of photovoltaic devices or semiconductor polymers. Furthermore, said bis-thienobenzothienothiophene compounds, after functionalization, may be advantageously used as spectral converters in luminescent solar concentrators.

21 Claims, No Drawings

(56) References Cited

OTHER PUBLICATIONS

"Efficient Synthesis of a Reqioreqular Oliqothiophene Photovoltaic Dye Molecule, MK-2, and Related Compounds: A Cooperative Hypervalent Iodine and Metal-Catalyzed Synthetic Route", Chemistry—A European Journal (2013), vol. 19, No. 6, p. 2067-2075.

BIS-THIENOBENZOTHIENOTHIOPHENE COMPOUNDS AND PROCESS FOR THEIR PREPARATION

The present invention relates to new bis-thienobenzothienothiophene compounds and a process for their preparation.

More in particular, the present invention relates to bis-thienobenzothienothiophene compounds and the process for their preparation wherein said process comprises reacting at least one dihalogenated dithiophene compound with at least one terminal alkyne and the subsequent double annulation reaction. Said bis-thienobenzothienothiophene compounds may be appropriately functionalized and polymerized to produce electron donor compounds that can be advantageously used in the construction of photovoltaic devices, such as photovoltaic cells, photovoltaic modules, solar cells, solar modules, both on a rigid support and on a flexible support.

Furthermore said bis-thienobenzothienothiophene compounds may be advantageously used, after appropriate functionalization, as monomers for the preparation of semiconductor polymers.

A further application for the compounds according to the invention is in the field of LSCs—"Luminescent Solar Concentrators". In fact, when appropriately substituted, said compounds may be advantageously used as spectral converters.

Photovoltaic devices are devices able to convert the energy of light radiation into electrical energy. Currently, most of the photovoltaic devices that can be used for practical applications exploit the chemical/physical properties of inorganic photoactive materials, in particular highly pure crystalline silicon. Due to the high production costs of silicon, however, scientific research has been focusing for some time on the development of alternative organic materials having a conjugated, oligomeric or polymeric structure, for the purpose of obtaining organic photovoltaic devices such as organic photovoltaic cells. In fact, unlike highly pure crystalline silicon, said organic materials are characterised in that they are relatively easy to synthesize, cheap to produce and the related organic photovoltaic devices are less heavy, as well as allowing said organic materials to be recycled at the end of the life cycle of the organic photovoltaic device in which they are used.

The advantages reported above make the use of said organic materials energetically and economically attractive despite potential lower efficiencies (i) of the organic photovoltaic devices thus obtained with respect to inorganic photovoltaic devices.

The operation of organic photovoltaic devices, such as organic photovoltaic cells, is based on the combined use of an electron acceptor compound and an electron donor compound. In the state of the art, the electron acceptor compounds most frequently used in organic photovoltaic devices are fullerene derivatives, in particular PC61BM (6,6-phenyl-$C_{61}$-butyric acid methyl ester) or PC71BM (6,6-phenyl-$C_{71}$-butyric acid methyl ester), which have led to the highest efficiencies when mixed with electron donor compounds chosen from n-conjugated polymers, such as polythiophenes ($\eta>5\%$), polycarbazoles ($\eta>6\%$), derivatives of poly(thieno-thiophene)-benzodithiophene (PTB) ($\eta>8\%$).

The elementary conversion process of light into electrical current in an organic photovoltaic cell takes place through the following stages:

1. Absorption of a photon by the electron donor compound with the formation of an exciton, i.e. a pair of "electron-electron hole" charge carriers.
2. Diffusion of the exciton in a region of the electron donor compound up to the interface with the electron acceptor compound;
3. Disassociation of the exciton in the two charge carriers: electron (−) in the accepting phase (i.e. in the electron acceptor compound) and electron hole (+)] in the donating phase (i.e. in the electron donating compound);
4. Carrying the charges thus formed at the cathode (electron through the electron acceptor compound) and at the anode [electron hole through the electron donor compound], with the generation of an electric current in the organic photovoltaic cell circuit.

The photoabsorption process with the formation of the exciton and subsequent loss of an electron to the electron acceptor compound implies the excitation of an electron from the HOMO ("Highest Occupied Molecular Orbital") to the LUMO ("Lowest Unoccupied Molecular Orbital") of the electron donor compound and, subsequently, the passage from this to the LUMO of the electron acceptor compound.

Since the efficiency of an organic photovoltaic cell depends on the number of free electrons generated by dissociation of the excitons in turn directly connected with the number of absorbed photons, one of the structural characteristics of electron donor compounds that affects such efficiency most strongly is the difference in energy between the HOMO and LUMO orbitals of the electron donor compound, i.e. the so-called "band-gap". This difference depends in particular on the maximum wave length at which the electron donor compound is able to harvest and effectively convert photons into electrical energy, i.e. the so-called "light harvesting" or "photon harvesting" process. In order to obtain acceptable electric currents the band gap, i.e. the difference in energy between HOMO and LUMO in the donor compound, must on one hand not be too high so as to allow the absorption of the highest number of photons but, on the other hand, not be too low as this could reduce the voltage at the electrodes of the device.

In the simplest operating method, the organic photovoltaic cells are made by introducing between two electrodes, usually made of indium tin oxide (ITO) (anode) and aluminium (Al) (cathode), a thin layer (about 100 nanometers) of a mixture of the electron acceptor compound and the electron donor compound (architecture known as "bulk heterojunction"). Generally, for the purpose of creating a layer of this type, a solution of the two compounds is prepared and, subsequently, a photoactive film is created on the anode [indium tin oxide (ITO)] based on said solution, making use of appropriate application techniques, such as "spin-coating", "spray-coating", "ink-jet printing", and the like. Finally, on the dried film, the counter electrode is deposited [i.e. the aluminium (Al) cathode]. Optionally, between the electrodes and the photoactive film, other additional layers may be introduced, which can perform specific electrical, optical or mechanical functions.

Generally, for the purpose of helping the electron holes to reach the anode [indium tin oxide (ITO)] and at the same time stop electrons being carried, hence improving the charge harvesting by the electrode and inhibiting recombination phenomena, before creating the photoactive film starting from the mixture of the acceptor compound and the donor compound as described above, a film is deposited, based on an aqueous suspension of PEDOT:PSS [poly(3,4-ethylenedioxythiophene)polystyrene sulfonate], making use of appropriate application techniques, such as "spin-coating", "spray-coating", "ink-jet printing", and the like. Finally, the counter electrode is deposited [(Al) cathode] on the dried film.

The most commonly used electron donor compound for the production of organic photovoltaic cells is regioregular poly(3-hexylthiophene) (P3HT). This polymer has excellent electronic and optical characteristics (good HOMO and LUMO orbital values, good molar absorption coefficient), good solubility in the solvents used to produce photovoltaic cells and discrete mobility of electron holes.

Other examples of polymers that can be advantageously used as electron donor compounds are: the polymer PCDTBT {poly[N-9"-heptadecanyl-2,7-carbazole-alt-5,5-(4',7'-di-2-thienyl-2',1',3'-benzothiadiazole]}, the polymer PCPDTBT {poly[2,6-(4,4-bis-(2-ethylhexyl)-4H-cyclopenta[2,1-b; 3,4-b']-dithiophene)-alt-4,7-(2,1,3-benzothiadiazole)]}. Electron donor compounds are also known containing benzothiophene units which have a similar structure to polyhexylthiophene (P3HT) but in which the thiophene units are planarized by benzene rings. This characteristic, as well as increasing the oxidation potential of said electron donor compounds, improves their stability in the air and guarantees their rapid packing and, therefore, high molecular order, during the production of the photoactive film. This translates into excellent charge carrying properties [electrons or electron holes]. Therefore, the use of electron donor compounds containing benzothiophene units can enable photovoltaic units with better performance levels to be produced.

For example, conjugated polymers, electron donors, containing the linear bis-thienobenzothienothiophene unit, are described by Mullen K. et al in the article: "Tetrathiahexacene as Building Block for Solution-Processable Semiconducting Polymers: Exploring the Monomer Size Limit", "*Macromolecules*" (2010), Vol. 43, pg. 6264-6267. Said article describes the preparation of a polymer containing the dithienodibenzothienothiophene unit which shows high stability against oxidation, in organic field effect transistors (OFET), and also high charge carrier mobility.

Another example of a conjugated polymer containing the linear bis-thienobenzothienothiophene unit is described by Biniek L. et al in the article: "New fused Bis-Thienobenzothienothiophene Copolymers and their Use in Organic Solar Cells and Transistors", "*Macromolecules*" 2013, Vol. 46, No. 3, pg. 727-735.

In the state of the art there are processes for the preparation of polycyclic aromatic compounds through aryl or heteroaryl annulation reactions with internal alkynes, in the presence of non-nucleophilic organic bases.

For example, Burton D. J. et al, in the article: "Site-Specific Preparation of 2-Carboalkoxy-4-substituted Naphthalenes and 9-Alkylphenanthrenes and Evidence for an Allene Intermediate in the Novel Base-Catalyzed Cyclization of 2-Alkynylbiphenyls", "Organic letters" (2006), Vol. 8, No. 23, pg. 5295-5298, describe an annulation reaction of internal aryl alkynes according to the following diagram 1:

Diagram 1

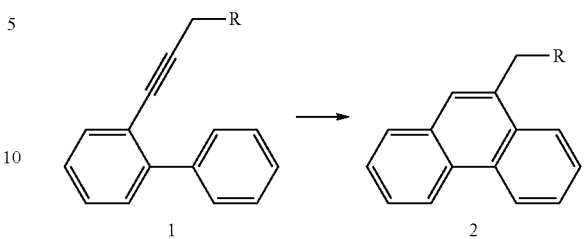

wherein an internal aryl alkyne having formula (1), such as 2-alkynyl-biphenyl, is reacted in the presence of a non-nucleophilic organic base, such as 1,8-Diazabicyclo[5,4,0] undec-7-ene (DBU), of a solvent such as 1-methyl-2-pyrrolidone (NMP), at a temperature of 200° C., obtaining a monosubstituted phenanthrene having formula (2).

The Applicant has now found that through annulation reactions of appropriate bis-alkynylarylene compounds it is possible to prepare new polycyclic compounds characterised in that they contain bis-thienobenzothienothiophene units with an angular shape fused together, stable in the air which, through functionalization and polymerization, provide polymers with excellent packing of the chains and therefore high charge mobility. Therefore a first subject matter of the present invention is a bis-thienobenzothienothiophene compound having general formula (I):

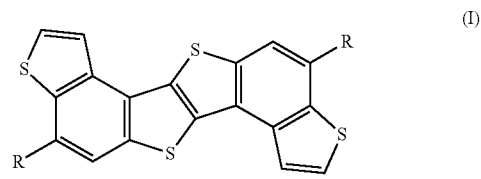

(I)

wherein:
R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted.

For the purpose of the present description and following claims, the definitions of the numeric ranges always include the extremes unless specified otherwise.

The term "$C_1$-$C_{20}$ alkyl group" means an alkyl group having from 1 to 20 carbon atoms, linear or branched. The term "cycloalkyl group" means a cycloalkyl group preferably having from 3 to 10 carbon atoms.

Said alkyl or cycloalkyl groups may be optionally substituted with one or more groups, the same or different from one another, chosen from: halogen atoms, such as fluorine, chlorine, preferably fluorine, hydroxyl groups, $C_1$-$C_{20}$ alkyl groups, $C_1$-$C_{20}$ alkoxy groups, cyano groups, amine groups, nitro groups.

Specific examples of $C_1$-$C_{20}$ alkyl groups are: methyl, ethyl, n-propyl, iso-propyl, n-butyl, iso-butyl, t-butyl, pentyl, ethyl-hexyl, hexyl, heptyl, octyl, nonyl, decyl, dodecyl.

Specific examples of cycloalkyl groups are: cyclopropyl, 2,2-difluorocyclopropyl, cyclobutyl, cyclopentyl, cyclohexyl, methylcyclohexyl, methoxicyclohexyl, fluorocyclohexyl, phenylcyclohexyl.

The new fused angular compounds of formula (I) can be prepared through the annulation of the related bis-alkynylarylene precursors.

Therefore the subject matter of the present invention is also a process for the preparation of bis-thienobenzoarylene compounds having general formula (I):

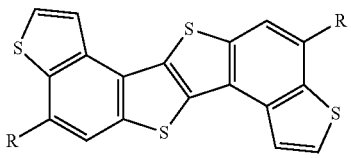
(I)

wherein:

R represents a hydrogen atom, a linear or branched $C_1$-$C_{20}$ alkyl group, preferably $C_1$-$C_{12}$, or a cycloalkyl group, where said alkyl groups or cycloalkyl groups are optionally substituted, where said process comprises reacting at least one bis-alkynylarylene compound having general formula (II):

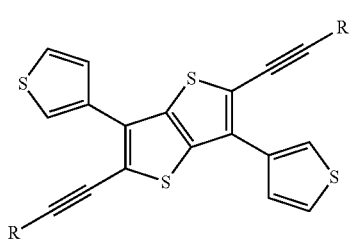
(II)

wherein R has the same meaning described above, with a non-nucleophilic organic base.

For the purpose of the present description and following claims, the definitions of the numeric ranges always include the extremes unless specified otherwise.

The term "$C_1$-$C_{20}$ alkyl group" means an alkyl group having from 1 to 20 carbon atoms, linear or branched.

The term "cycloalkyl group" means a cycloalkyl group preferably having from 3 to 10 carbon atoms.

Said cycloalkyl group may be optionally substituted with one or more groups, the same or different from one another, chosen from: halogen atoms, such as fluorine, chlorine, preferably fluorine, hydroxyl groups, $C_1$-$C_{20}$ alkyl groups, $C_1$-$C_{20}$ alkoxy groups, cyano groups, amine groups, nitro groups.

Specific examples of $C_1$-$C_{20}$ alkyl groups are: methyl, ethyl, n-propyl, iso-propyl, n-butyl, iso-butyl, t-butyl, pentyl, ethyl-hexyl, hexyl, heptyl, octyl, nonyl, decyl, dodecyl.

Specific examples of cycloalkyl groups are: cyclopropyl, 2,2-difluorocyclopropyl, cyclobutyl, cyclopentyl, cyclohexyl, methylcyclohexyl, methoxicyclohexyl, fluorocyclohexyl, phenylcyclohexyl.

The aforementioned process therefore corresponds to the following diagram 2:

Diagram 2

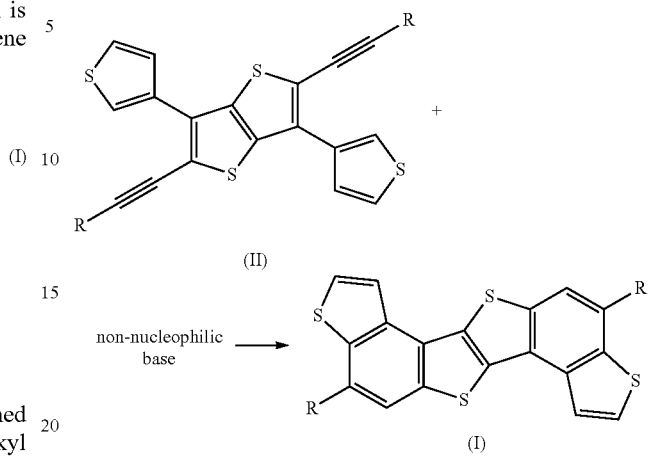
(I)

wherein R has the same meaning described above.

In accordance with a preferred embodiment of the present invention, said bis-alkynylarylene compound having general formula (II) and said non-nucleophilic organic base can be used in molar ratios comprised between 1:1 and 1:5, preferably comprised between 1:1 and 1:3.

In accordance with a preferred embodiment of the present invention, said non-nucleophilic organic based is preferably chosen from 1,8-diazabicyclo[5,4,0]undec-7-ene (DBU) and 1,4-diazabicyclo[2.2.2]octane (DABCO).

Preferably, said non-nucleophilic organic base is 1,8-diazabicyclo[5,4,0]undec-7-ene (DBU).

In accordance with a preferred embodiment of the present invention, said process can be performed in presence of at least one dipolar aprotic organic solvent.

In accordance with a preferred embodiment of the present invention, said dipolar aprotic organic solvent can be chosen, for example, from: N,N-dimethyl acetamide (DMAc), dimethyl sulfoxide (DMSO), N-methyl pyrrolidone (NMP), N,N-dimethylformamide (DMF), or mixtures thereof. Preferably, said dipolar aprotic organic solvent is N-methyl pyrrolidone (NMP).

In accordance with a preferred embodiment of the present invention, said bis-alkynylarylene compound having general formula (II) can be used at a molar concentration comprised between 0.02 M and 0.1 M mmoles, preferably comprised between 0.04 M and 0.08 M.

In accordance with a preferred embodiment of the present invention, said process can be performed at a temperature comprised between 120° C. and 220° C., preferably comprised between 180° C. and 210° C.

In accordance with a preferred embodiment of the present invention, said process can be performed for a time comprised between 30 minutes and 5 hours, preferably comprised between 1 hour and 3 hours.

In accordance with a preferred embodiment of the present invention, reported in diagram 3, said process relates to the preparation of 4,10-bis(3,7-dimethyloctyl)-benzo[b]tiophene-[5',4'-2,3]thiophene[4,5-b]tihophene[3,2-e]benzo[b]thiophene (Ia) corresponding to a bis-thienobenzoarylene compound having general formula (I) wherein R represents a 3,7-dimethyloctyl compound, where said compound (Ia) is new and is particularly the subject matter of the present invention.

The preparation process of compound (Ia) comprises reacting 2,5-bis(5,9-dimethyldec-1-inyl)-3,6-di(3-thienyl)thiophene[3,2-b]thiophene (IIa), corresponding to a bis-alkynylarylene compound having general formula (II) wherein R represents a 3,7-dimethyloctyl group, with a non-nucleophilic organic base, preferably 1,8-Diazabicyclo[5,4,0]undec-7-ene (DBU), as reported in the following diagram:

Diagram 3

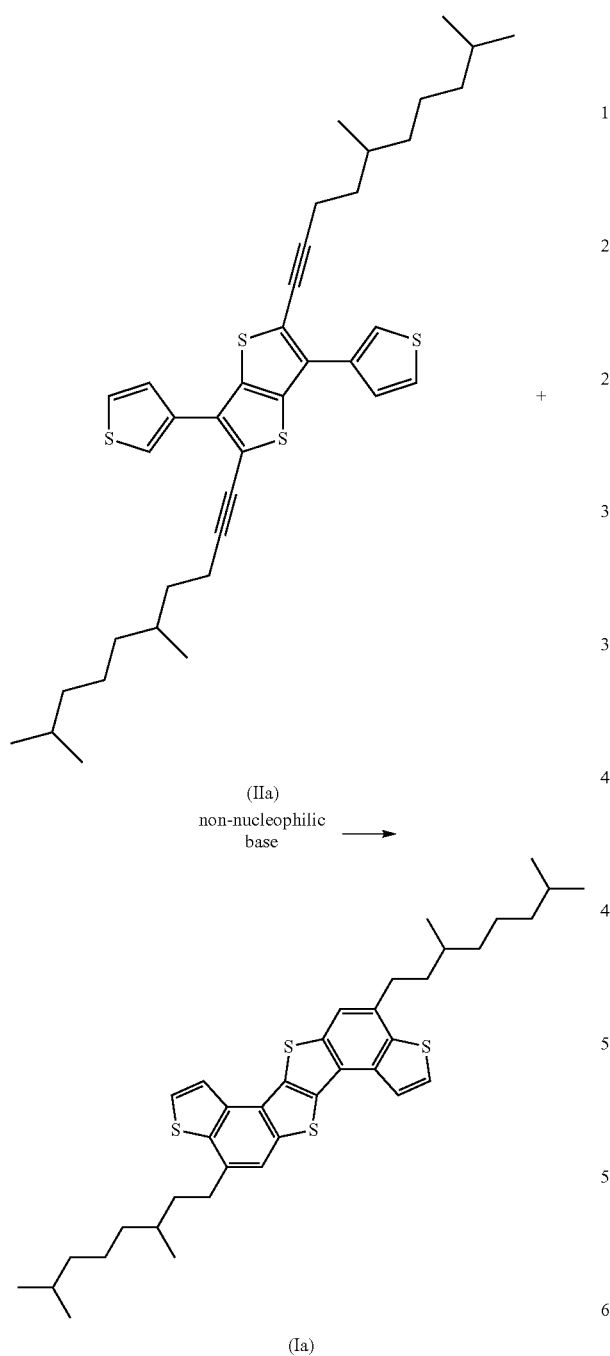

(IIa)
non-nucleophilic base →

(Ia)

In accordance with a preferred embodiment of the present invention, said process relates to the preparation of 4,10-bis(2-decyltetradecyl)benzo[b]thiophene[5',4'-2,3]thiophene[4,5-b]thiophene[3,2-e]benzo[b]thiophene (Ib) corresponding to a bis-thienobenzothieno-thiophene compound having general formula (I) wherein R represents a 2-decyltetradecyl compound, where said compound (Ib) is new and is particularly the subject matter of the present invention.

The preparation process of compound (Ib) comprises reacting 2,5-bis(4-decylhexadec-1-inyl)-3,6-di(3'-thienyl)thieno[3,2-b]thiophene (IIb), corresponding to a bis-alkynylarylene compound having general formula (II) wherein R represents a 2-decyltetradecyl group, with a non-nucleophilic organic base, preferably 1,8-Diazabicyclo[5,4,0]undec-7-ene (DBU), as reported in the following diagram:

Diagram 4

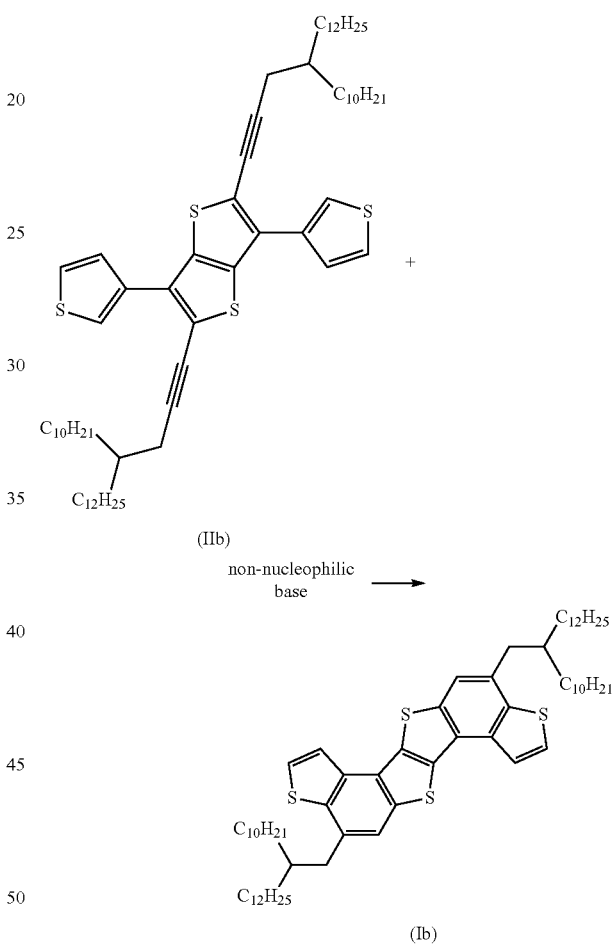

In general the bis-alkynylarylene compounds having general formula (II) can be obtained according to processes known in the state of the art, for example, through coupling reactions between halogenated dithiophene compounds, where the halogen is chosen from bromine and iodine, and terminal alkynes, catalysed by copper and palladium compounds. More details on said processes can be found, for example, in the article by Mullen K. et al: "Tetrathiahexacene as Building Block for Solution-Processable Semiconducting Polymers: Exploring the Monomer Size Limit", "*Macromolecules*" (2010), Vol. 43, pg. 6264-6267; in the article by Swager T. M. et al: "Direct Electrophilic Cyclizations: Efficient Methodology for the Synthesis of Fused Polycyclic Aromatics", "Journal of the American Chemical Society" (1997), Vol. 119, pg. 4578-4593; in the article by Rafael Chinchilla and Carmen Nájera (2007) "The Sonogashira Reaction: A Booming Methodology in Synthetic Organic Chemistry" Chem. Rev. *American Chemical Society* 103 (3): 874-922. DOI: 10.1021/cr050992x.

In general the coupling reaction, corresponding to the Sonogashira reaction, can be performed in an inert atmosphere, at a temperature comprised between 25° C. and 80° C., using a solvent chosen from toluene, tetrahydrofuran, dioxane and N,N-dimethylformamide, in the presence of an amide chosen from diethylamine, triethylamine and N,N-diisopropylamine. Compounds of copper and palladium that can be used are for example, respectively, copper (I) iodide [CuI] and bis(triphenylphosphine)-palladium(II)chloride [Pd(PPh$_3$)$_2$Cl$_2$].

The terminal alkynes used for the synthesis of the derivatives (II) can easily be obtained using synthetic methods present in literature. More details on said processes can be found, for example, in the article by Li Y. et al: "Synthesis of a polythieno[3,4-b]thiophene derivative with a low-lying HOMO level and its application in polymer solar cells", *"Chemical Communications"* (2011), Vol. 47, pg. 8850-8852.

The halogenated dithiophene compounds that react with alkynes are 2,5-dihalogeno-3,6-di(3'-thienyl)thieno[3,2-b]thiophene, where the halogen is chosen from bromine and iodine and in turn can be easily obtained from 3,6-di(3'-thienyl)thieno[3,2-b]thiophene (IV) using N-iodosuccinimide or N-bromosuccinimide, according to the halogen chosen to be included. The reaction is performed in an inert atmosphere at a temperature comprised between 25° C. and 40° C. in a solvent chosen from chloroform and dichloromethane, preferably chloroform, in the presence of an organic acid, for example acetic acid. Preferably the N-halogeno-succinimide is added in portions to the solution containing the 3,6-di(3'-thienyl)thieno[3,2-b]thiophene (IV) and the acid. The desired product 2,5-dihalogeno-3,6-di(3'-thienyl)thieno[3,2-b]thiophene precipitates and is isolated by filtration. The halogen present in the dithiophene compound used is preferably iodine. Said compounds 2,5-dihalogeno-3,6-di(3'-thienyl)thieno[3,2-b]thiophene, where the halogen is chosen from bromine and iodine, precursors of the compounds of formula (I), are new and are further subject matter of the present invention.

The 3,6-di(3'-thienyl)thieno[3,2-b]thiophene (IV) is easily prepared from 3,6-dihalogenothieno[3,2-b]thiophene, where the halogen is chosen from bromine and iodine, through synthetic methods present in literature: more details on said processes can be found, for example, in the article by C. Ko, W. H. Lam, V. W. Yam—Chem. Com. 2008, 5203. Preferably dibromothieno[3,2-b]thiophene (V) is used.

In general the preparation, which corresponds to a Suzuki coupling, can be performed for example in dioxane, in the presence of sodium carbonate and tetrakis(triphenylphosphine)-palladium, in an inert atmosphere and at a temperature comprised between 80° C. and 120° C.

The 3,6-dihalogenothieno[3,2-b]thiophene, preferably 3,6-dibromothieno[3,2-b]thiophene (V), is prepared from the corresponding 2,3,5,6-tetrahalogenothieno[3,2-b]thiophene, preferably 2,3,5,6-tetrabromothieno[3,2-b]thiophene (VI), as described, for example, in Fuller et al. J. Chem. Soc. Perkin Trans. 1, 1997, 3465, or in M. Turbiez et al. Chem. Comm. 2005, 1161.

In general the reaction can be performed easily by reacting 2,3,5,6-tetrabromothieno[3,2-b]thiophene (VI) with zinc powder in the presence of acetic acid at a temperature comprised between 60° C. and 100° C.

The 2,3,5,6-tetrahalogenothieno[3,2-b]thiophenes can be prepared as described in J. Chem. Soc. Perkin Trans. 1, 1997, 3465 and Chem. Comm. 2005, 1161.

In particular, the 2,3,5,6-tetrabromothieno[3,2-b]thiophene (VI) is easily prepared from thienothiophene (VII) by bromination as described, for example, in Fuller et al. J. Chem. Soc. Perkin Trans. 1, 1997, 3465, or in M. Turbiez et al. Chem. Comm. 2005, 1161. In accordance with the above a method of synthesis of the angular monomer bis-thienobenzothienothiophene (I) according to the present invention is described in diagram 5. It envisages an initial polybromination reaction of the thienothiophene unit (VII) obtaining the polybrominated derivative (VI), subsequent selective debromination of the positions α,α' obtaining the derivative (V), Suzuki coupling reaction, for example with 3-thienylboronic acid, producing the derivative (IV), double iodination to produce the compound (III), Sonogashira reaction with the appropriate terminal alkyne to produce the derivative (II) and finally the key step to produce the desired molecule (I) by means of a double cyclization reaction induced by a non-nucleophilic organic base, for example diazabicycloundecene (DBU):

Diagram 5

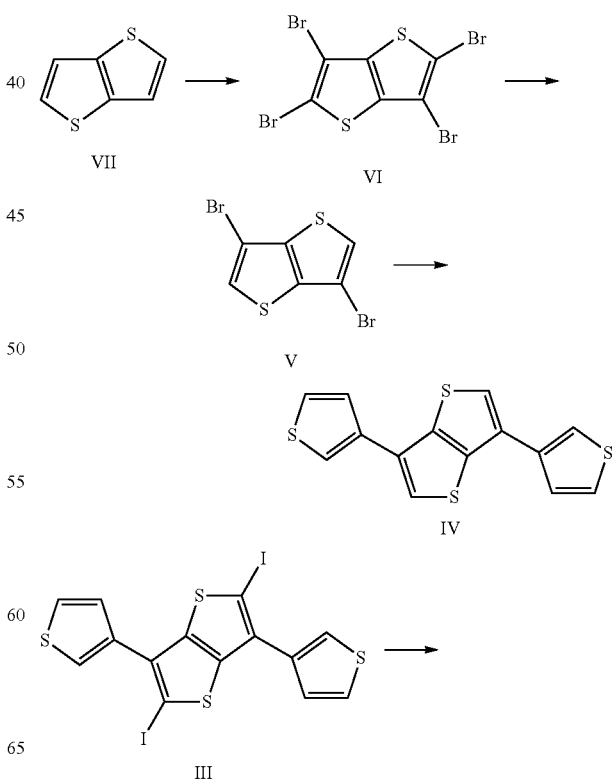

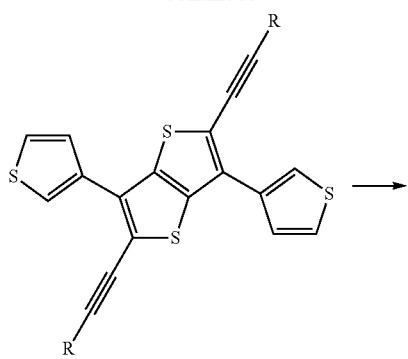

II

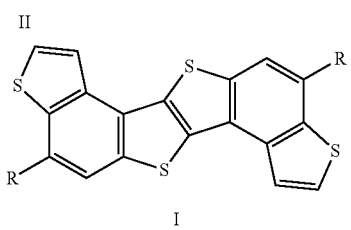

I

Said bis-thienobenzoarylene compounds of formula (I) may be appropriately functionalized and then polymerized, to produce semiconductors or electron donor compounds that can be advantageously used in the construction of photovoltaic devices, such as photovoltaic cells, photovoltaic modules, solar cells, solar modules, both on a rigid support and on a flexible support.

The functionalization of the compound of formula (I) can take place in the α positions of the thiophene ring, through the insertion of two reactive groups. All the reactive groups known to a person skilled in the art can be used to functionalize the compound of formula (I). In particular, according to a preferred aspect, the monomers thus obtained can have one of the following formulae (Im), (In) and (Io):

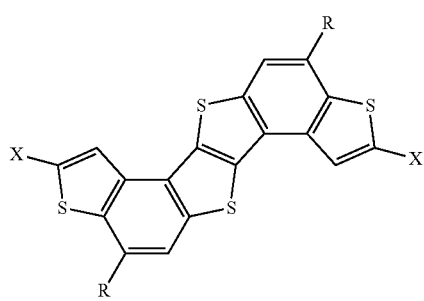
(Im)

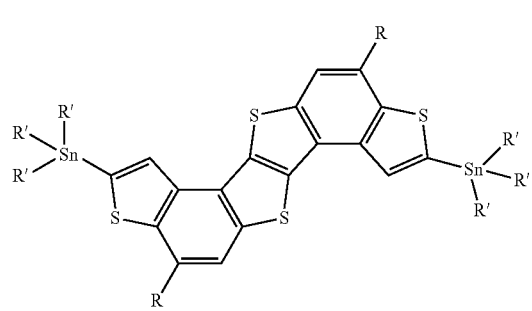
(In)

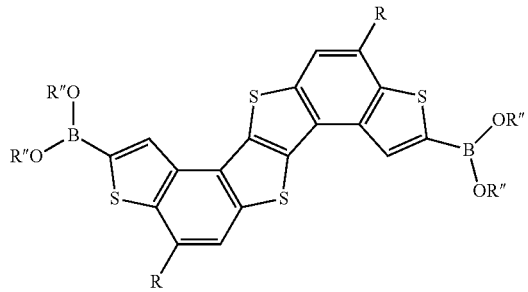
(Io)

where:
  R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted,
  X is selected from chlorine, bromine and iodine, and is preferably bromine,
  R', identical or different, represent linear or branched $C_1$-$C_{20}$ alkyl groups,
  R", identical or different, represent a hydrogen atom, or a linear or branched $C_1$-$C_{20}$ alkyl group, or the groups OR" together with other atoms to which they are linked may form a heterocyclic ring having the following formula (1):

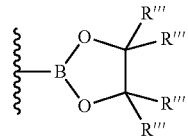
(1)

in which the substituents R''', identical or different, represent a hydrogen atom, or a linear or branched $C_1$-$C_{20}$ alkyl group,
  B is boron, and
  Sn is tin.

Said monomers (Im), (In) and (Io) are new and are further subject matter of the invention. The monomer (Im) may be subjected to polymerization, for example, with monomers having one of the following formulae 1a or 1b:

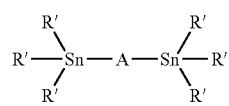
1a

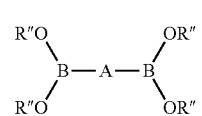
1b

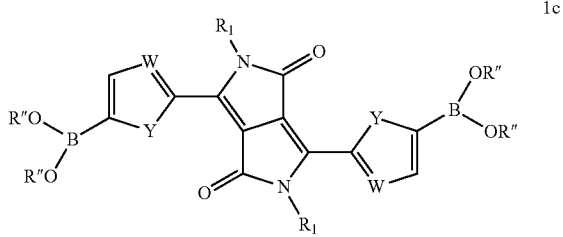
1c wherein:
Sn is tin
B is boron
A represents a heteroarylene group, penta- or hexa-atomic, even benzocondensed or heterobicyclic, containing from 1 to 4 heteroatoms chosen from nitrogen, oxygen, sulfur, silicon, selenium, phosphorus, such as, thiophenylene, 3,4-dialkylthiophenylene, 3,4-dialkoxythiophenylene, 2,7-(9,9-dialkyl)fluorenylene, 3,6-(9-alkyl)carbazolene, 2,7-(9-alkyl)carbazolene, 4,7-(2-alkyl)benzo-2,1,3-triazolene, 10-alkyl-acridolene, wherein alkyl represents a linear or branched $C_1$-$C_{20}$ alkyl group, preferably $C_2$-$C_{10}$, and alkoxy represents a linear or branched $C_1$-$C_{20}$, alkoxy group, preferably $C_2$-$C_{10}$; or
A represents an arylene group, said arylene group optionally being substituted with one or more groups chosen from —C(R$_A$)$_3$ and —COR$_A$ wherein R$_A$, identical or different among them, represent a hydrogen atom or a linear or branched $C_1$-$C_{20}$ alkyl group, preferably $C_2$-$C_{10}$; or with one or more linear or branched $C_1$-$C_{20}$ alkyl groups, preferably $C_2$-$C_{10}$; or with one or more aryl groups;
R', identical or different, represent a linear or branched $C_1$-$C_{20}$ alkyl group,
R", identical or different, represent a hydrogen atom, or a linear or branched $C_1$-$C_{20}$ alkyl group, or the groups OR" together with other atoms to which they are linked may form a heterocyclic ring having the following formula (1):

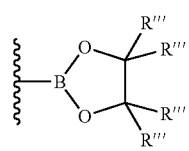

(1)

wherein the substituents R''', identical or different, represent a hydrogen atom, or a linear or branched $C_1$-$C_{20}$ alkyl group.

The compound of formula (1c) is a special monomer belonging to the monomers having general formula 1b reported above, where:
R$_1$ represents a linear or branched $C_1$-$C_{20}$ alkyl group, preferably $C_2$-$C_{10}$, or linear or branched $C_1$-$C_{20}$ alkoxy group, preferably $C_2$-$C_{10}$;
Y is chosen from oxygen, sulfur, selenium and an NR$_Y$ group wherein R$_Y$ represents a hydrogen atom, or a linear or branched $C_1$-$C_{20}$ alkyl group, preferably $C_2$-$C_{10}$;
W is chosen from oxygen and nitrogen.

The term "arylene groups" means divalent carbocyclic aromatic groups. Said carbocyclic aromatic groups can be optionally substituted, with one or more substituents chosen from halogen, for example, fluorine, chlorine, preferably fluorine; hydroxyl groups; $C_1$-$C_{20}$ alkoxyl groups; cyane groups; amino groups; nitro groups. Specific examples of arylene groups are: phenylene, methylphenylene, trimethylphenylene, methoxyphenylene, hydroxyphenylene, phenyloxyphenylene, fluorophenylene, pentafluorophenylene, chlorophenylene, nitrophenylene, dimethylaminophenylene, naphthylene, phenylnaphthylene, phenanthrenylene, anthracenylene.

When the monomer (Im) is polymerized with the monomers of formula 1a or 1b, the resulting polymer will contain units of formula (Ipa):

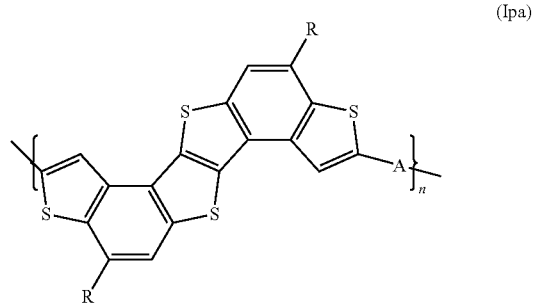

(Ipa)

where:
R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted, and
A has the meanings described above in relation to the monomers 1a and 1b.

When the monomer (Im) is polymerized with itself the resulting polymer will contain units of formula (Ip):

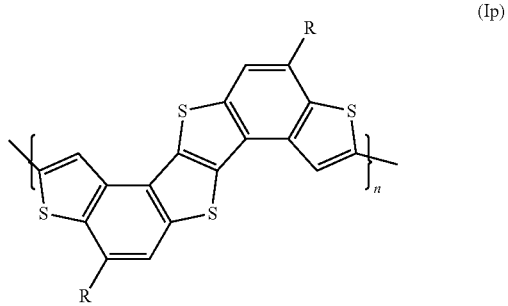

(Ip)

where R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted.

The monomers of formula (In) or (Io) can be subjected to polymerization, e.g. with monomers of formula X-A-X, where:
A represents a heteroarylene group, penta- or hexa-atomic, even benzocondensed or heterobicyclic, containing from 1 to 4 heteroatoms chosen from nitrogen, oxygen, sulfur, silicon, selenium, phosphorus, such as, thiophenylene, 3,4-dialkylthiophenylene, 3,4-dialkoxythiophenylene, 2,7-(9,9-dialkyl)fluorenylene, 3,6-(9-alkyl)carbazolene, 2,7-(9-alkyl)carbazolene, 4,7-(2-alkyl)benzo-2,1,3-triazolene, 10-alkyl-acridolene, wherein alkyl represents a linear or branched $C_1$-$C_{20}$ alkyl group, preferably $C_2$-$C_{10}$, and alkoxy represents a linear or branched $C_1$-$C_{20}$, alkoxy group, preferably $C_2$-$C_{10}$; or
A represents an arylene group, said arylene group optionally being substituted with one or more groups chosen from —C(R$_A$)$_3$ and —COR$_A$ wherein R$_A$, identical or different among them, represent a hydrogen atom or a linear or branched $C_1$-$C_{20}$ alkyl group, preferably $C_2$-$C_{10}$; or with one or more linear or branched $C_1$-$C_{20}$ alkyl groups, preferably $C_2$-$C_{10}$; or with one or more aryl groups;

X represents a halogen atom chosen from chlorine, fluorine, bromine, iodine, preferably bromine.

Special monomers of formula X-A-X may be as follows:

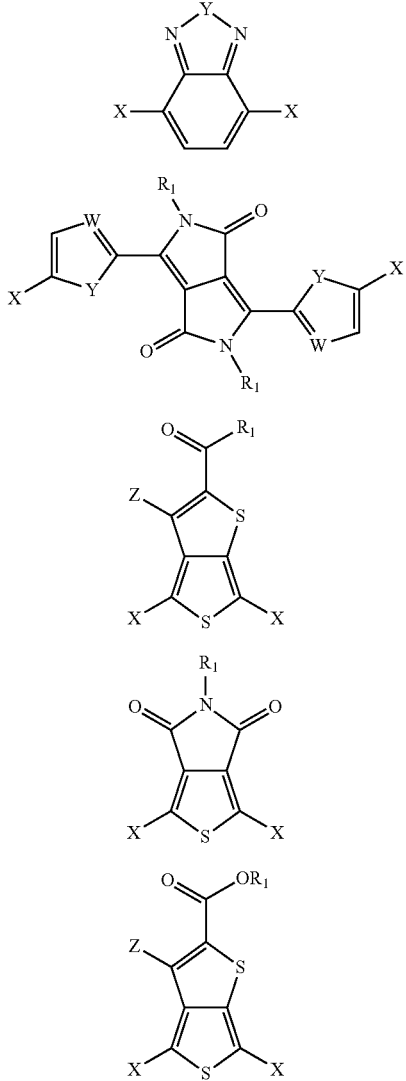

where:
- $R_1$ represents a linear or branched $C_1$-$C_{20}$ alkyl group, preferably $C_2$-$C_{10}$, or a linear or branched $C_1$-$C_{20}$ alkoxy group, preferably $C_2$-$C_{10}$;
- Y is chosen from oxygen, sulfur, selenium and NR wherein R represents a hydrogen atom, or a linear or branched $C_1$-$C_{20}$ alkyl group, preferably linear or branched $C_2$-$C_{10}$;
- W is chosen from oxygen and nitrogen,
- R', identical or different, represent a linear or branched $C_1$-$C_{20}$ alkyl group,
- Z represents a hydrogen atom or a fluorine atom.

When the monomers (In) and (Io) are polymerized with the monomers X-A-X, in particular with the monomers of formula 2a, 2b, 2c, 2d or 2e, the resulting polymer will contain units of formula (Ipa)

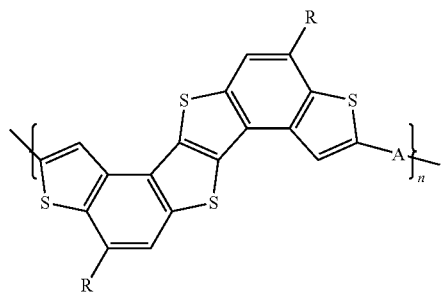

where:
R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted, A has the same meanings described above for the monomer X-A-X.

Polymers containing the unit (Ip) or the unit (Ipa) are new and are further subject matter of the invention, as is their use as semiconductor polymers or electron donor compounds for photovoltaic devices.

All the functionalizations of the compounds of formula (I) and the reactions of the monomers thus obtained, e.g. with the monomers of formulae 1a, 1b, 1c, 2a, 2b, 2c, 2d, 2e and X-A-X, can be performed according to techniques known to a person skilled in the art, e.g. as described in "Tetrathiahexacene as Building Block for Solution-Processable Semiconducting Polymers: Exploring the Monomer Size Limit", "*Macromolecules*" (2010), Vol. 43, pg. 6264-6267 and in Biniek L. et al "New fused Bis-Thienobenzothienothiophene Copolymers and their Use in Organic Solar Cells and Transistors", "*Macromolecules*" 2013, Vol. 46, No. 3, pg. 727-735; or in "13-Alkyl substituted Dithieno[2,3-d; 2',3'-d']benzo[1,2-b; 4,5-b']dithiophene Semiconducting Materials and Their Application to Solution-Processed Organic Transistors", "*Chemistry of Materials*" (2010), Vol. 24, No. 17, pg. 3464-3472.

The bis-thienobenzothienothiophene compounds of formula (I) according to the present invention can also be appropriately monofunctionalized in just one of the α positions and then be advantageously used as intermediate products in the synthesis of spectral converters in LSCs—Luminescent Solar Concentrators. All the functionalizations known to a person skilled in the art can be used. Such monofunctionalized intermediate products can, for example, have the following formulae I1, I2 and I3, reported below:

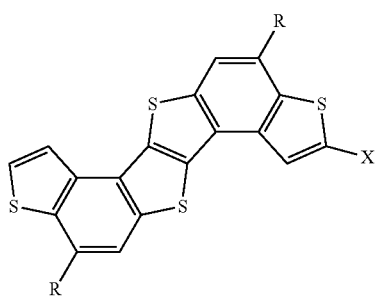

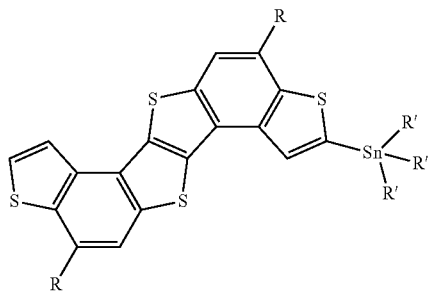

(12)

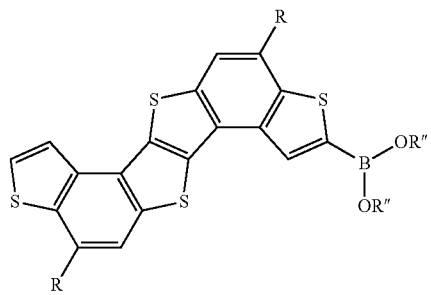

(13)

where:
- R represents a hydrogen atom, a linear or branched, $C_1$-$C_{20}$ alkyl group, preferably $C_1$-$C_{12}$, or a cycloalkyl group, where said alkyl groups or cycloalkyl groups are optionally substituted,
- X is selected from chlorine, bromine or iodine, preferably bromine,
- R', identical or different, represent a linear or branched $C_1$-$C_{20}$ alkyl group;
- R", identical or different, represent a hydrogen atom, or a linear or branched $C_1$-$C_{20}$ alkyl group, or the groups OR" together with other atoms to which they are linked may form a heterocyclic ring having the following formula (1):

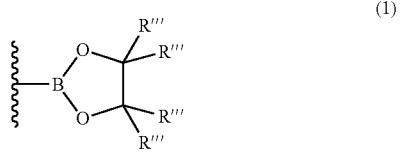

(1)

in which the substituents R''', identical or different, represent a hydrogen atom, or a linear or branched $C_1$-$C_{20}$ alkyl group, and B is boron.

Said intermediate products of formula (I1a), (I2) and (I3) are new and are further subject matter of the present invention.

The insertion of said substituents X, Sn(R')$_3$ and B(OR")$_3$ in the structure of (I) can be performed according to the techniques known to a person skilled in the art, e.g. in "Synthesis and Properties of a Series of Well-Defined and Polydisperse Benzo[1,2-b:4,3-b']dithiophene Oligomers", "*The Journal of Organic Chemistry*" (2007), Vol. 72, No. 24, pg 9141-9151; or in "Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility", "*Chemistry of Materials*" (2012), Vol. 24, No. 10, pg 1699-1709; or in "*Efficient Synthesis of a Regioregular Oligothiophene Photovoltaic Dye Molecule, MK-2, and Related Compounds: A Cooperative Hypervalent Iodine and Metal-Catalyzed Synthetic Route*", "*Chemistry—A European Journal*" (2013), Vol. 19, No. 6, pg 2067-2075.

Said intermediate compounds I1, I2 and I3 reported above can be advantageously used in the synthesis of LSCs—Luminescent Solar Concentrators. For example solar concentrators that can be prepared using said intermediate products I1, I2 and I3 can have the following general formula (4a):

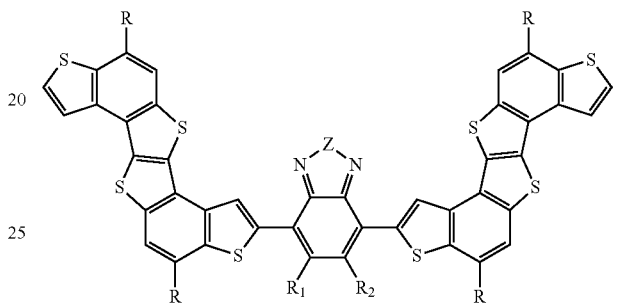

(4a)

wherein:
- Z represents a heteroatom selected from oxygen (O), sulfur (S) and selenium (Se), and is preferably sulfur (S);
- R represents a hydrogen atom, a $C_1$-$C_{20}$ alkyl group, preferably $C_1$-$C_{12}$, linear or branched, or a cycloalkyl group, where said alkyl groups or cycloalkyl groups are optionally substituted,
- $R_1$, $R_2$, identical or different, represent a hydrogen atom; or are chosen from $C_1$-$C_{20}$ alkyl groups, preferably $C_2$-$C_{10}$, linear or branched, optionally substituted cycloalkyl groups, optionally substituted aryl groups, $C_1$-$C_{20}$ akoxyl groups, preferably $C_2$-$C_{10}$, linear or branched; or $R_1$ and $R_2$ may optionally be linked so as to form, along with the carbon atoms to which they are linked, a cycle or polycyclic system containing 2 to 14 carbon atoms, preferably 4 to 6 carbon atoms, saturated, unsaturated, or aromatic, optionally containing one or more heteroatoms such as, for example, oxygen, sulfur, nitrogen, silicon, phosphorus, selenium.

Said compounds can be obtained by reacting one of the compounds of formula I1, I2 or I3 with a compound of formula (L)

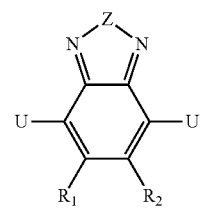

(L)

wherein the substituents U are B(OR")$_2$ groups when the intermediate product is I1, and are halogen when the intermediate product is I2 or I3, where:

R', identical or different, represent a linear or branched $C_1$-$C_{20}$ alkyl group;

R", identical or different, represent a hydrogen atom, or a linear or branched $C_1$-$C_{20}$ alkyl group, or the groups OR" together with other atoms to which they are linked may form a heterocyclic ring having the following formula (1):

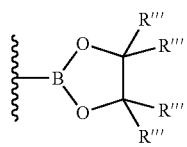
(1)

wherein the substituents R'", identical or different, represent a hydrogen atom, or a linear or branched $C_1$-$C_{20}$ alkyl group.

The reaction between the intermediate products I1, I2 and I3 with the compound of formula (L) can be performed for example as described in "Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility", *Chemistry of Materials* (2012), Vol. 24, No. 10, pg 1699-1709; or in *"Efficient Synthesis of a Regioregular Oligothiophene Photovoltaic Dye Molecule, MK-2, and Related Compounds: A Cooperative Hypervalent Iodine and Metal-Catalyzed Synthetic Route"*, *Chemistry—A European Journal* (2013), Vol. 19, No. 6, pg 2067-2075; or in "Benzodithiophene derivatives and their use as Photoluminescent Compounds", "WO2013098726 (A1)" The compounds thus obtained are in turn subject matter of the invention as is their use as solar converters.

For the purpose of understanding the present invention better and to put it into practice, below are some illustrative and non-limitative examples thereof.

EXAMPLE 1

Preparation of 2,3,5,6-tetrabromothieno[3,2-b]thiophene having formula (VI) in diagram 5

The preparation is performed in accordance with L. S. Fuller, B. Iddon, K. A. Smith—*J. Chem. Soc. Perkin Trans.* 1 1997, 3465 and M. Turbiez, P. Frere, P. Leriche, N. Mercier, J. Roncali—*Chem. Comm.* 2005, 1161).

In an inert atmosphere, the bromine (9.2 ml; 28.5 g; 178.2 mmoles) diluted in 40 ml of chloroform is added to a solution of thienothiophene (5 g; 35.7 mmoles) in 40 ml of chloroform, by slow dripping. The temperature is brought to 60° C. After 24 hours, it is brought to 20° C. and a 1M aqueous solution of sodium thiosulfate is added until the excess bromine is completely destroyed. The precipitate is filtered and washed first with water and then with chloroform. 14.6 g of 2,3,5,6-tetrabromothieno[3,2-b]thiophene of formula (VI) are obtained with a 91% yield:

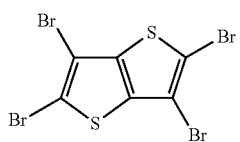
VI

EXAMPLE 2

Preparation of 3,6-dibromothieno[3,2-b]thiophene having formula (V) in diagram 5

In an inert atmosphere, the zinc powder (3.5 g; 53.5 mmoles) is added in portions to the suspension of 2,3,5,6-tetrabromothieno[3,2-b]thiophene (14.6 g; 32.2 mmoles) in 1 l of acetic acid. It is brought to 125° C. After 2 hours another portion of zinc is added (2.2 g; 33.6 mmoles) and after 30 minutes another portion (0.8 g; 12.2 mmoles). It is brought to 70° C. and the zinc is removed by filtration. At 20° C., water is added to the filtrate and extracted with ethyl acetate. After washing the organic phase, first with a saturated aqueous solution of sodium bicarbonate and then to neutrality with water, it is dried over sodium sulfate. 7.6 g of 3,6-dibromothieno[3,2-b]thiophene of formula (V) are obtained with a 80% yield:

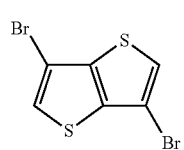
V

EXAMPLE 3

Preparation of 3,6-bis(3'-thienyl)thieno[3,2-b]thiophene having formula (IV) in diagram 5

The preparation is performed in accordance with C. Ko, W. H. Lam, V. W. Yam—*Chem. Com.* 2008, 5203.

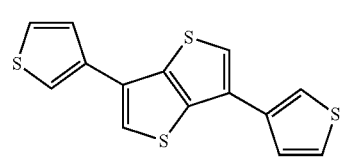
IV

EXAMPLE 4

Preparation of 2,5-diiodo-3,6-di(3'-thienyl)thieno[3,2-b]thiophene having formula (III) in diagram 5

In at inert atmosphere, at 35° C., the N-iodosuccinimide (8.6 g; 38.1 mmoles) is added, in portions, to the solution of 3,6-bis(3'-thienyl)thieno[3,2-b]thiophene (5.8 g; 19.02 mmoles) in 1 l of chloroform and 100 ml of acetic acid. After 10 hours at 25° C. in the dark, a 1M aqueous solution of sodium thiosulfate is added. After filtration and washing of the precipitate first with water and then with ethyl ether, 8.9 g of 2,5-diiodo-3,6-di(3'-thienyl)thieno[3,2-b]thiophene of formula (III) are obtained with a yield of 85%:

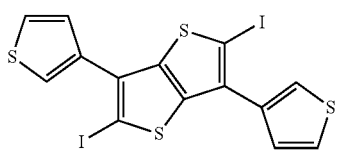

(III)

EXAMPLE 5

Preparation of 2,5-bis(5,9-dimethyldec-1-inyl)-3,6-di(3-thienyl)thieno[3,2-b]thiophene having formula (IIa)

In a 100 ml Pyrex glass flask, equipped with a cooling device, in an inert atmosphere, the following are loaded, in order: (2.7 g; 4.80 mmoles) of 2,5-diiodo-3,6-di(3'-thienyl)thieno[3,2-b]thiophene (5), 50 ml of toluene, 10 ml di triethylamine, (2.4 g; 14.40 mmoles) of 5,9-dimethyldecine, (0.064 g, 0.096 mmoles) of bis(triphenylphosphine)palladium(II)chloride [Pd(PPh$_3$)$_2$Cl$_2$] and (0.018 g, 0.096 mmoles) of copper(I)iodide (CuI). The flask is then placed in an oil bath pre-heated to 80° C., for 24 hours. After cooling to room temperature (25° C.), a saturated aqueous solution of sodium chloride (50 ml) is added to the reaction mixture and everything is extracted with diethyl ether (3×25 ml). The organic phase obtained is washed to neutrality with water (3×25 ml), and then dried over sodium sulfate and evaporated. The residue obtained is purified through elution on a silica gel chromatography column (eluent: heptane), obtaining 2.55 g of 2,5-bis(5,9-dimethyldec-1-inyl)-3,6-di(3-thienyl)thieno[3,2-b]thiophene as a white solid (85% yield):

iodide (CuI). The flask is then placed in an oil bath pre-heated to 80° C., for 24 hours. After cooling to room temperature (25° C.), a saturated aqueous solution of sodium chloride (50 ml) is added to the reaction mixture and everything is extracted with diethyl ether (3×25 ml). The organic phase obtained is washed to neutrality with water (3×25 ml), and then dried over sodium sulfate and evaporated. The residue obtained is purified through elution on a silica gel chromatography column (eluent: heptane), obtaining 2.51 g of 2,5-bis(4-decylhexadec-1-inyl)-3,6-di(3'-thienyl)thieno[3,2-b]thiophene as a white solid (51% yield):

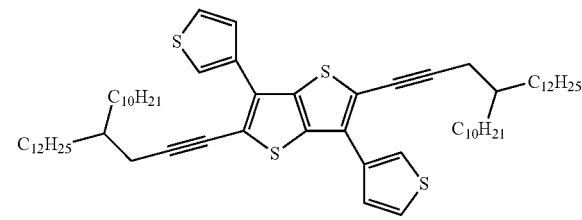

(IIb)

EXAMPLE 7

Preparation of 4,10-bis(3,7-dimethyloctyl)benzo[b]thieno[5',4'-2,3]thieno[4,5-b]thieno[3,2-e]benzo[b]thiophene having formula (Ia)

In an inert atmosphere, 1,8-Diazabicyclo[5,4,0]undec-7-ene (DBU), (0.33 g; 2.14 mmoles) was added to a solution of 2,5-bis(5,9-dimethyldec-1-inyl)-3,6-di(3'-thienyl)thieno[3,2-b]thiophene having formula (IIa) (1.2 g; 1.78 mmoles) in 20 ml of N-methyl pyrrolidone (NMP). The reaction is then placed in an oil bath pre-heated to 200° C., for 3 hours. After cooling to room temperature (25° C.), the reaction mixture is placed in 100 mL of methanol, the precipitate obtained is filtered and dried under vacuum, obtaining 0.90 g of 4,10-bis(3,7-dimethyloctyl)benzo[b]thieno[5',4'-2,3]thieno[4,5-b]thieno[3,2-e]benzo[b]thiophene as a white solid (yield 80%):

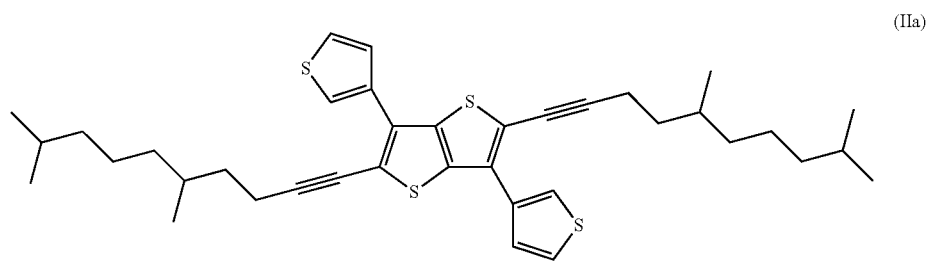 [SMILES: CC(C)CCCC(C)CCC#Cc1sc2c(-c3ccsc3)c(C#CCCC(C)CCCC(C)C)sc2c1-c1ccsc1]

(IIa)

EXAMPLE 6

Preparation of 2,5-bis(4-decylhexadec-1-inyl)-3,6-di(3-thienyl)thieno[3,2-b]thiophene having formula (IIb)

In a Pyrex glass flask, equipped with a cooling device, in an inert atmosphere, the following are loaded, in order: (2.7 g; 4.80 mmoles) of 2,5-diiodo-3,6-di(3'-thienyl)thieno[3,2-b]thiophene (5), 50 ml of toluene, 10 ml di triethylamine, (5.2 g; 14.40 mmoles) of 4-hexadecyldecine, (0.064 g, 0.096 mmoles) of bis(triphenylphosphine)palladium(II)chloride [Pd(PPh$_3$)$_2$Cl$_2$] and (0.018 g, 0.096 mmoles) of copper(I)

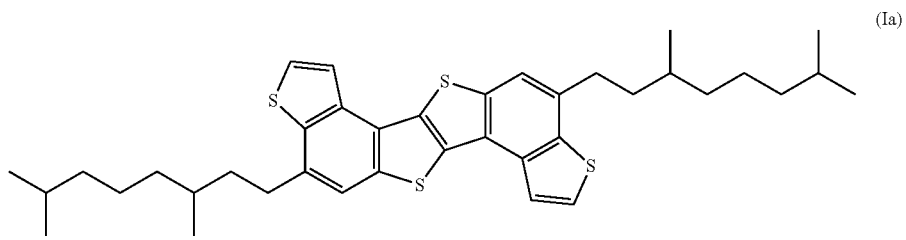 [SMILES: CC(C)CCCC(C)CCc1cc2sc3c(sc4cc(CCC(C)CCCC(C)C)c5sccc5c43)c2c2ccsc12]
(Ia)

EXAMPLE 8

Preparation of 4,10-bis(2-decyltetradecyl)benzo[b]thiophene[5',4'-2,3]thiophene[4,5-b]thiophene[3,2-e]benzo[b]thiophene having formula (Ib)

In an inert atmosphere, 1,8-Diazabicyclo[5,4,0]undec-7-ene (DBU), (0.23 g; 1.68 mmoles) is added to a solution of 2,5-bis(4-decylhexadec-1-inyl)-3,6-di(3'-thienyl)thieno[3,2-b]thiophene having formula (IIb) (1.4 g; 1.40 mmoles) in 20 ml of N-methyl pyrrolidone (NMP). The reaction is then placed in an oil bath pre-heated to 200° C., for 3 hours. After cooling to room temperature (25° C.), the reaction mixture is placed in 100 mL of methanol, the precipitate obtained is filtered and dried under vacuum, obtaining 1.14 g of 4,10-bis(3,7-dimethyloctyl)benzo[b]thieno[5',4'-2,3]thieno[4,5-b]thieno[3,2-e]benzo[b]thiophene of formula (Ib) as a white solid (yield 81%):

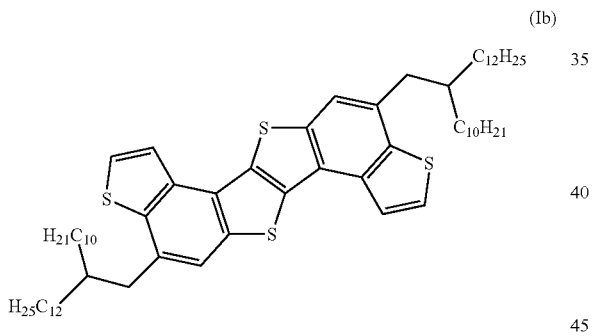
(Ib)

The invention claimed is:

1. Bis-thienobenzothienothiophene compound having the general formula (I):

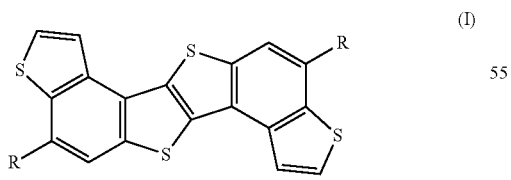
(I)

where R is selected from hydrogen, $C_1$-$C_{20}$ alkyl group, linear or branched, or cycloalkyl group, where said alkyl and cycloalkyl groups are optionally substituted.

2. Compound according to claim 1 in which R is a $C_1$-$C_{12}$ alkyl group.

3. Compound according to claim 1 wherein R is a $C_3$-$C_{10}$ cycloalkyl group.

4. Compound according to claim 1 in which R is 3,7-dimethyloctyl.

5. Compound according to claim 1 in which R is 2-decyltetradecyl.

6. Monomers having one of the following formulas (Im), (In) or (Io), where:

R represents a hydrogen atom, a linear or branched, $C_1$-$C_{20}$ alkyl group, or a cycloalkyl group, where said alkyl groups or cycloalkyl groups are optionally substituted, X is selected from chlorine, bromine and iodine, R', identical or different, represent alkyl groups $C_1$-$C_{20}$ linear or branched, R" identical or different, represent a hydrogen atom, or a linear or branched $C_1$-$C_{20}$ alkyl group, or the OR" groups together with other atoms to which they are linked may form a heterocyclic ring having the following formula (1):

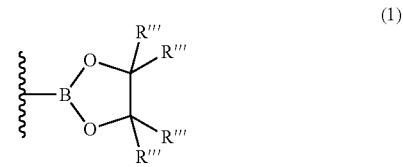
(1)

in which the substituents R'", identical or different, represent a hydrogen atom, or a linear or branched $C_1$-$C_{20}$ alkyl group, B is boron, and Sn is tin,

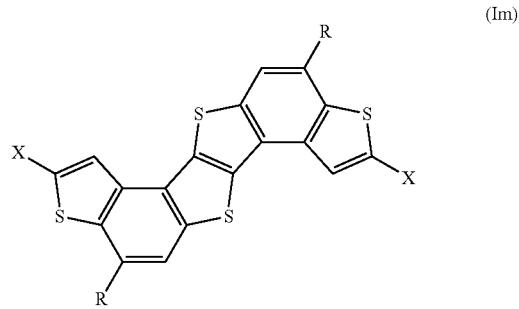
(Im)

(In)

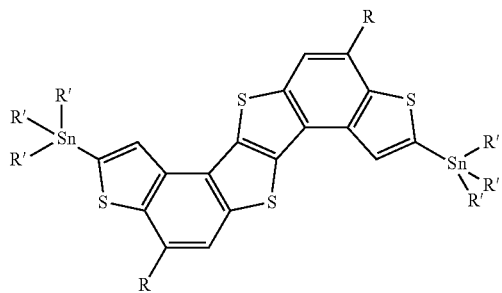

(Io)

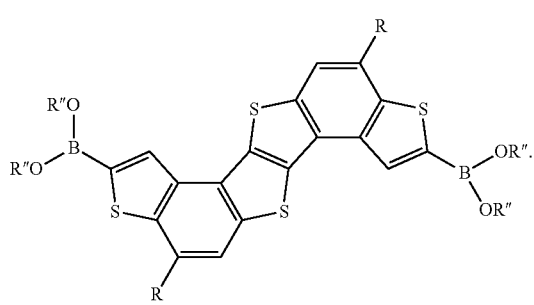

7. Compounds having the following formulas I1, I2 and I3:

(I1)

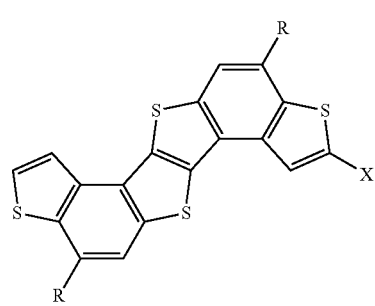

(I2)

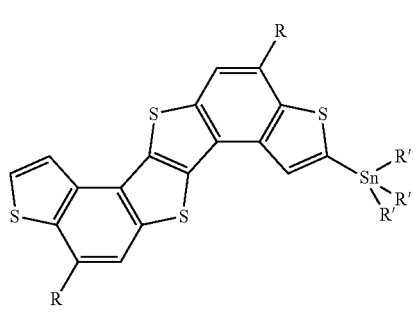

(I3)

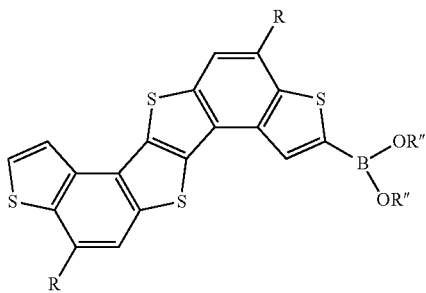

where:
- R represents a hydrogen atom, a linear or branched $C_1$-$C_{20}$ alkyl group, or a cycloalkyl group, where said alkyl groups or cycloalkyl groups are optionally substituted,
- X is selected from chlorine, bromine and iodine,
- R', identical or different, represent a linear or branched $C_1$-$C_{20}$ alkyl group,
- R″, identical or different, represent a hydrogen atom, or a linear or branched $C_1$-$C_{20}$ alkyl group, or the OR″ groups together with other atoms to which they are linked may form a heterocyclic ring having the following formula (1):

(1)

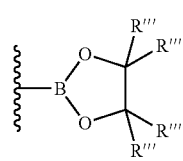

in which the substituents R‴, identical or different, represent a hydrogen atom, or a linear or branched $C_1$-$C_{20}$ alkyl group,
B is boron, and
Sn is tin.

8. Compounds of formula (4a)

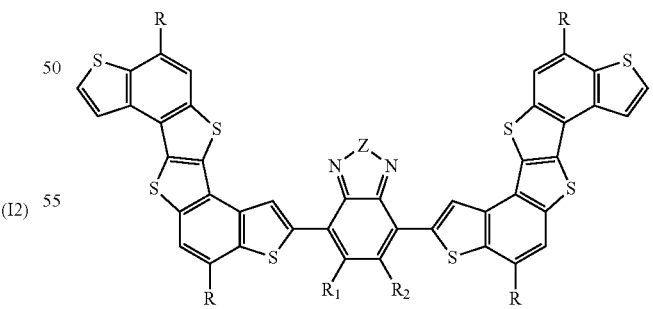

in which:
- Z represents a heteroatom selected from oxygen (O), sulphur (S) and selenium (Se);
- R represents a hydrogen atom, a linear or branched $C_1$-$C_{20}$ alkyl group, or a cycloalkyl group, where said groups are optionally substituted alkyl or cycloalkyl, $R_1$, $R_2$, identical or different, represent a hydrogen atom; or are selected from a linear or branched $C_1$-$C_{20}$ alkyl group, optionally substituted cycloalkyl groups, aryl groups, optionally substituted, linear or branched $C_1$-$C_{20}$ alkoxy groups, or $R_1$ and $R_2$ are linked together so as to form, together with the carbon atoms to which they are linked a cycle, or a polycyclic system containing from 2 to 14 carbon atoms, saturated, unsaturated or aromatic, optionally containing one or more heteroatoms.

9. Process for the preparation of bis-thienobenzothienothiophene compounds having general formula (I):

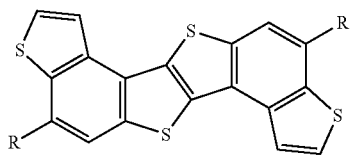
(I)

comprising reacting with a non-nucleophilic organic base at least one bis-alkynylarylene compound having general formula (II):

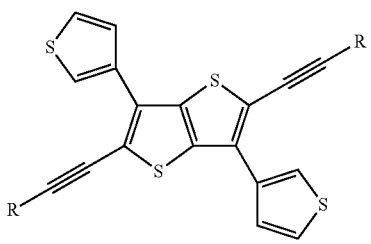
(II)

in which:

R represents a hydrogen atom, a linear or branched $C_1$-$C_{20}$ alkyl group, or a cycloalkyl group, where said groups are optionally substituted alkyl or cycloalkyl.

10. The process according to claim 9 wherein the compound of general formula (II) and the non-nucleophilic organic base are used in molar ratios ranging between 1:1 and 1:5.

11. The process according to claim 9, wherein the non-nucleophilic organic base is selected from 1,8-diazabicyclo [5,4,0] undec-7-ene (DBU) and 1,4-diazabicyclo [2.2.2] octane (DABCO).

12. The process according to claim 11 wherein the base is 1,8-diazabicyclo [5,4,0] undec-7-ene (DBU).

13. The process according to claim 9 conducted in the presence of at least dipolar aprotic organic solvent.

14. The process according to claim 9 conducted at a temperature between 120° C. and 220° C.

15. The process according to claim 9 in which the compound (II) is prepared by coupling reaction between 2,5-dihalo-3,6-di (3'-thienyl)thieno [3,2-b]thiophene, where the halogen is selected from bromine and iodine and a terminal alkyne of formula RCCH catalyzed by compounds of copper and palladium.

16. Compound of formula (III)

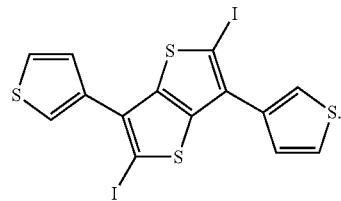
III

17. The compounds of claim 8 which are luminescent solar concentrators.

18. A polymer formed by a method comprising polymerizing at least one of the monomers (Im), (In) and (Io) according to claim 6.

19. The polymer according to claim 18 which is a semiconducting polymer or an electron donor for photovoltaic devices.

20. A method of making a polymer comprising polymerizing the monomer (Im) according to claim 6 with at least one of the following monomers having formula 1a or 1b:

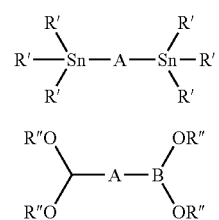
1a

1b wherein:

Sn is tin;

B is boron;

A represents a heteroarylene group containing from 1 to 4 heteroatoms chosen from nitrogen, oxygen, sulfur, silicon, selenium, phosphorus; or A represents an arylene group, said arylene group optionally being substituted with one or more groups chosen from —C($R_A$)$_3$ and —CO$R_A$ wherein $R_A$, identical or different among them, represent a hydrogen atom or a linear or branched $C_1$-$C_{20}$ alkyl group; or with one or more linear or branched $C_1$-$C_{20}$ alkyl groups; or with one or more aryl groups;

R', identical or different, represent a linear or branched $C_1$-$C_{20}$ alkyl group, R", identical or different, represent a hydrogen atom, or a linear or branched $C_1$-$C_{20}$ alkyl group, or the groups OR" together with other atoms to which they are linked may form a heterocyclic ring having the following formula (1):

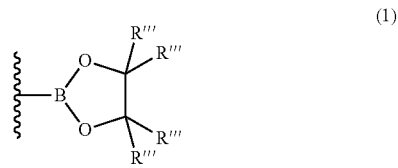
(1)

wherein the substituents R''', identical or different, represent a hydrogen atom, or a linear or branched $C_1$-$C_{20}$ alkyl group.

21. A method of making a polymer comprising polymerizing at least one of the monomers of formula (In) or (Io) according to claim 6, with monomers of formula X-A-X, where:

A represents a heteroarylene group containing from 1 to 4 heteroatoms chosen from nitrogen, oxygen, sulfur, silicon, selenium, phosphorus; or A represents an arylene group, said arylene group optionally being substituted with one or more groups chosen from —$C(R_A)_3$ and —$COR_A$ wherein $R_A$, identical or different among them, represent a hydrogen atom or a linear or branched $C_1$-$C_{20}$ alkyl group; or with one or more linear or branched $C_1$-$C_{20}$ alkyl groups; or with one or more aryl groups;

X represents a halogen atom.

* * * * *

UNITED STATES PATENT AND TRADEMARK OFFICE
CERTIFICATE OF CORRECTION

PATENT NO. : 9,920,067 B2
APPLICATION NO. : 15/535079
DATED : March 20, 2018
INVENTOR(S) : Gabriele Bianchi and Giuliana Schimperna It is certified that error appears in the above-identified patent and that said Letters Patent is hereby corrected as shown below:

Column 28, Lines 31-34, Formula 1b should appear as follows:

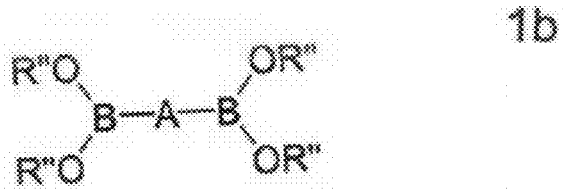

Signed and Sealed this
Tenth Day of July, 2018

Andrei Iancu
*Director of the United States Patent and Trademark Office*